United States Patent [19]

Hartmann

[11] 3,996,376
[45] Dec. 7, 1976

[54] HALOGENATED DIOXOLANE TRANQUILIZERS

[75] Inventor: Ludwig A. Hartmann, Wilmington, Del.

[73] Assignee: ICI United States Inc., Wilmington, Del.

[22] Filed: Apr. 3, 1975

[21] Appl. No.: 564,745

Related U.S. Application Data

[60] Division of Ser. No. 238,956, March 28, 1972, which is a continuation-in-part of Ser. No. 235,025, March 15, 1972, abandoned.

[52] U.S. Cl. .............................. 424/278; 260/340.9; 260/349
[51] Int. Cl.$^2$ .......................................... A01N 9/28
[58] Field of Search ................ 260/340.9; 424/278

[56] References Cited

UNITED STATES PATENTS

| | | | |
|---|---|---|---|
| 2,260,261 | 10/1941 | Morey | 260/340.9 |
| 2,589,296 | 3/1952 | Schroeder | 260/340.9 |
| 2,901,514 | 8/1959 | Drysdale | 260/615 |
| 2,911,414 | 11/1959 | Simmons | 260/340.9 |
| 2,925,424 | 2/1960 | Simmons | 260/340.9 |
| 3,058,981 | 10/1962 | Avakian et al. | 260/340.9 |
| 3,121,094 | 2/1964 | Horrom et al. | 260/340.9 |
| 3,246,012 | 4/1966 | Feit | 260/340.9 |
| 3,285,936 | 11/1966 | Gilbert et al. | 260/340.9 |
| 3,314,850 | 4/1967 | Gilbert | 260/340.9 |
| 3,324,144 | 6/1967 | Coe et al. | 260/340.9 |
| 3,379,736 | 4/1968 | Dietrich et al. | 260/340.9 |
| 3,404,162 | 10/1968 | Selman | 260/340.9 |
| 3,467,674 | 9/1969 | Braun | 260/340.9 |
| 3,475,456 | 10/1969 | Selman | 260/340.9 |
| 3,488,335 | 1/1970 | Braun | 260/340.9 |
| 3,547,951 | 12/1970 | Hardie et al. | 260/340.9 |
| 3,597,435 | 8/1971 | Houlihan | 260/340.9 |
| 3,741,986 | 6/1973 | Hartmann | 260/340.9 |
| 3,749,794 | 7/1973 | Terrell et al. | 260/340.9 |
| 3,812,261 | 5/1974 | Hartmann | 260/340.9 |

FOREIGN PATENTS OR APPLICATIONS

| | | |
|---|---|---|
| 697,590 | 4/1967 | Belgium |
| 1,445,013 | 7/1966 | France |
| 2,312,963 | 10/1973 | Germany |
| 6,609,579 | 1/1967 | Netherlands |
| 225,215 | 8/1968 | U.S.S.R. |

OTHER PUBLICATIONS

Ellison et al., Toxicology & App. Pharm. 18, 69–82 (1971).
Boekelheide et al., J. Amer. Chem. Soc., 71, 3303–3307 (1949).
Chaldt et al., Acta Biol. et Med. Germ. 15, 79–88 (1965).
Hibbert et al. J. Amer. Chem. Soc., 45, 734–751 (1923).
Vystral et al., Chem. Listy, 44, 204–210 (1950), C. A. 45:7956A.
Yasmitskii et al., Bhurn. Obsh. Khim., 34, 1940–1945 (1964), C. A. 61: 8180 (1964).
Yoder, J. Amer. Chem. Soc. 45, 475–479 (1923).
Barubinskii et al., Bhurn. Obsh. Khim., 35 (9), 1624–1627 (1965).
Barubinskii et al., Bhurn. Obschei Khimii, 36(6), 1031–1017, 1966.
Barubinskii et al., Bhurn. Obschei Khimii, 35(10), 1790–1798 (1965).
Simmons et al., Journ. Amer. Chem. Soc., 82, 2288–2296 (1960).
Melson, Acta Biol. Med. Ger., 6, 395–406 (1961).
Melson, Acta Biol. Med. Germ. 8, 381–386 (1962).
Melson, Arzneimittel–Forsch, 13, 23–26 (1963).

*Primary Examiner*—Ethel G. Love

[57] ABSTRACT

Halogenated dioxolane compounds having perhalogenated groups in the 2-position and other substituted groups, for example, carbamate and nitrate in the 4 and/or 5-position are disclosed. These compounds are useful as tranquilizers.

16 Claims, No Drawings

HALOGENATED DIOXOLANE TRANQUILIZERS

This is a division of application Ser. No. 238,956, filed Mar. 28, 1972, which in turn is a continuation-in-part of my copending United States Application Ser. No. 235,025, filed Mar. 15, 1972, entitled "HALOGENATED DIOXOLANE TRANQUILIZERS", now abandoned.

This invention relates to novel halogenated dioxolane compounds and to their method of preparation and use.

The compounds of the present invention have the following general formula

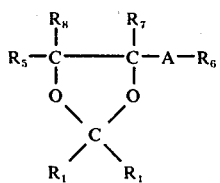

wherein each $R_1$ is an independently selected perhalogenated alkyl radical, A is an alkylene radical, $R_6$ is selected from the group consisting of

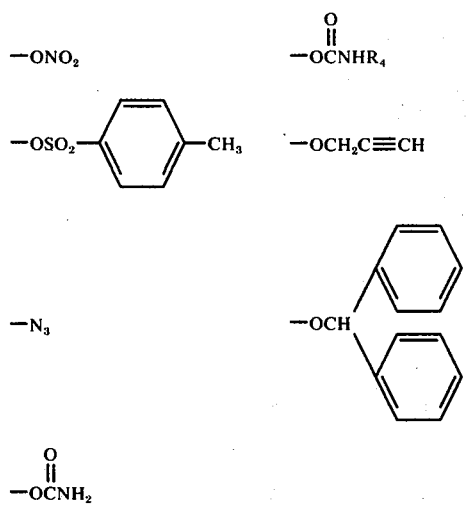

$R_6$ can be positioned at the end of "A" (alkylene radical) or anywhere along its length. $R_4$ is selected from the group consisting of lower alkyl radicals, phenyl, tolyl, halophenyl, and cyclohexyl. $R_5$ is selected from the group consisting of hydrogen, alkyl and —A—$R_6$. $R_7$ and $R_8$ are independently selected from the group consisting of hydrogen and lower alkyl radicals. It is also within the scope of the present invention that $R_6$ can be a hydroxyl radical when either $R_7$ or $R_8$ is an alkyl radical or when the total number of carbon atoms in the alkylene or alkyl chains contained in the radicals represented by —A— and $R_5$ combined equal 6 or more.

Pharmacological studies indicate that the dioxolane compounds of the present invention are useful as tranquilizers in living animal bodies or more specifically mammalian bodies. More particularly, the subject compounds which are central nervous system depressants are considered to be principally minor tranquilizers in that they share many pharmacologic properties with the barbiturates and are useful in the treatment of nervousness and for producing tranquilization.

A preferred group of compounds coming within formula (1) above are those wherein each $R_1$ is independently selected from the group consisting of perhalogenated alkyl radicals having the formula $C_nX_{2n+1}$ wherein n is an integer from 1 to 7 and X is a halogen atom having an atomic weight of at most 80. In a preferred species X is fluorine or chlorine or any combination thereof. It is intended that the subject compounds can be substituted with perhalogenated alkyl groups containing mixed halogens such as for example, dichlorofluoromethyl groups which are symmetrical (meaning that both $R_1$ groups are identical), as well as perhalogenated alkyl groups which are unsymmetrical, e.g., 2-chlorodifluoromethyl-2-dichlorofluoromethyl. Obviously the subject $R_1$ groups can also be unmixed perhalogenated alkyl groups which are either symmetrical or unsymmetrical.

In another preferred embodiment of the present invention —A— in the above formula (1) represents a linear or non-linear alkylene radical containing from 1 to 18 carbon atoms with the proviso that the combined total number of carbon atoms in the alkylene or alkyl chains contained in the radicals represented by —A— and $R_5$ is not more than 18 and with the further proviso that the alkylene or alkyl chains contained in the radical represented by $R_5$ contain no more than 6 carbon atoms.

It has been determined that a further preferred group of compounds coming within formula (1) above is obtained when —A— represents either linear or non-linear alkylene radicals containing from 1 to 6 atoms. $R_5$ in formula (1) in a preferred group of compounds represents, other than hydrogen and —A—$R_6$, lower alkyl radicals containing from 1 to 6 carbon atoms. Further $R_4$ is an alkyl radical containing from 1 to 4 carbon atoms and the halogen constituent of the halophenyl radical is chlorine or fluorine. In a preferred species the said halophenyl radical is p-halophenyl. In the present group of compounds $R_7$ and $R_8$ independently represent, other than hydrogen, lower alkyl radicals containing from one to four carbon atoms.

The novel dioxolane compounds of this invention advantageously can be prepared from a group of hydroxyl substituted cyclic ketals disclosed in U.S. Pat. Application Ser. No. 873,660 filed Nov. 3, 1969, now U.S. Pat. No. 3,741,986. The entire contents of this application (Ser. No. 873,660) is hereby incorporated by reference. Claim 1 of U.S. Pat. application Se. No. 873,660 is as follows:

1. A cyclic ketal of a polyhydric alcohol which contains at least three carbon atoms and at least three hydroxyl groups and a ketone represented by the formula

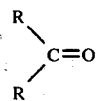

wherein each R is an halogenated alkyl radical containing at most three unhalogenated carbon atoms, and the carbon atom of said alkyl radical attached to the carbonyl atom of said ketone contains at least two halogen atoms, and said halogen has an atomic weight of at most 36.

A group of cyclic ketals coming within the above noted patent application which are most useful in the preparation of the dioxolane compounds of the present invention are those represented by the following formula (2)

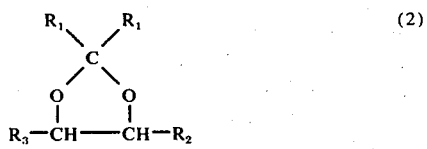 (2)

where each $R_1$ is a perhaloalkyl radical, $R_2$ and $R_3$ are independently selected from hydrogen, an alkyl radical, a hydroxyalkyl or polyhydroxyalkyl radical. In formula (2), $R_2$ and $R_3$ are chosen so that there is at least one free hydroxyl group.

In a subclass of the cyclic ketal of formula (2), each $R_1$ would be independently selected from perhaloalkyl radicals of from 1 to 7 carbon atoms and contain halogen atoms having an atomic weight of at most about 36. The $R_2$ and $R_3$ radicals of this class would be an alkyl radical, a hydroxyalkyl or polyhydroxyalkyl radical, or a hydrogen atom.

The preparation of the cyclic ketals of application Ser. No. 873,660 may be carried out by heating a ketone, having a formula

 (a)

wherein each R is a halogenated alkyl radical containing at most three unhalogenated carbon atoms and the carbon atom of said alkyl radicals attached to the carbonyl carbon of said ketone has at least two halogen atoms attached thereto, with a cyclic carbonate of a polyhydric alcohol, which polyhydric alcohol contains at least three hydroxyl groups and three carbon atoms, and which cyclic carbonate contains one or more cyclic carbonate groups. When said cyclic carbonate contains no free hydroxyl groups the reaction is carried out in the presence of a lower alcohol or water. The mol ratio of ketone to cyclic carbonate may be as high as about 10 mols of ketone per cyclic carbonate group. Where a lower alcohol is used a sufficient quantity for dissolving the cyclic carbonate is employed. Alternately, the cyclic ketals may be prepared by reacting a lower alcohol or water with a ketone within formula (a) above, forming a hydrate or a hemiketal respectively, and subsequently reacting this product with a cyclic carbonate described above. Where a cyclic carbonate containing more than one carbonate group is reacted products may be formed containing both carbonate and ketal rings.

Suitable polyhydric alcohols for carrying out the above reaction are, for examples, alkanetriols, alkanetetrols, alkanepentols and alkanehexols. More specifically, compounds such as sorbitol, mannitol, erythritol, xylitol, glycerol, 1,2,3-butanetriol, 1,2,3,4-hexanetetrol, 2,3,4-hexanetriol, 1,2,3-hexanetriol, 1,2,4-hexanetriol, 1,2,3-heptanetriol, 1,3,4-heptanetriol, 1,2,4-pentanetriol, 2-methyl-2,3,4-pentanetriol, and 1,2,4-butanetriol are considered within the class of polyhyric alcohols which contain at least three hydroxyl groups and at least three carbon atoms. A preferred group of polyhydric alcohols have from three to six carbon atoms and contain no more than one hydroxyl group per carbon atom. For example this group includes glycerol, sorbitol, threitol, erythritol, butanetriols and xylitol.

Ketones within formula (a) may, for example, preferably include perhalogenated alkyl radicals of the general formula $C_nX_{2n+1}$ where n is an integer from 1 to 7 and X is a halogen with an atomic weight of at most 80, more preferably 36. The halogen content of said ketones can be a mixture of halogens.

Examples of these ketones are bis(trifluoromethyl) ketone; bis(chlorodifluoromethyl) ketone; chlorodifluoromethyl dichlorofluoromethyl ketone; bis(pentafluoroethyl) ketone; bis(dichlorotrifluoroethyl) ketone; 1,1,1-tribromo-3,3,3-trifluoropropanone; and 3,3-dibromo-1,1,1,3-tetrafluoroacetone.

More particularly, a hydroxyl bearing cyclic carbonate of a polyhydric alcohol may be reacted with a ketone within formula (a) above in a two step reaction to form the cyclic ketal. The first step of the reaction forms an intermediate product which is a hemiketal of the ketone. This reaction may be initiated at temperatures as low as about 10° C. or as high as about 120° C. As the temperature falls below 10° C. initiation and reaction will become more difficult, as the temperature exceeds 120° C. the reaction proceeds progressively poorer and loss of the intermediate product results. The final reaction step is mostly an intramolecular reaction where the hemiketal function attached to said cyclic carbonate reacts with a carbonate group to form the cyclic ketal. This step, depending upon the reactants, will usually take at least one hour. The temperatures for this step are generally from 100° C. to about 170° C. As the temperature falls below 100° C. the reaction becomes sluggish; as the temperature rises above 170° C. loss of yield and reactants will start to occur.

An alternate process to yield compounds of formula (2) above which does not require the cyclic carbonate to also contain a free hydroxyl group, starts by reacting a ketone within formula (a) with a lower alcohol to form a hemiketal or with water to form a hydrated ketone. This reaction occurs at temperatures from about 10° to about 120° C. Then the product, namely the hydrate or hemiketal is reacted with a cyclic carbonate at from about 100° C. to about 170° C. to form the cyclic ketal; as in the above process the temperature ranges are chosen to optimize the reaction. Naturally if a suitable hemiketal or hydrate is available the formation step can be omitted and it can be directly reacted with the carbonate.

In a preferred method of preparing these ketals the mols of ketone per cyclic carbonate group are from about 0.3 to about 3, the cyclic carbonate used contains up to about 3 cyclic carbonate groups and at leaast one free hydroxyl group. The temperature is maintained at 25°–70° C. for from 0.5 to 30 hours and then raised to 120°–160° C. until carbon dioxide is no longer being evolved.

Among the lower alcohols which may be used are saturated aliphatic monohydric alcohols, saturated aliphatic diols, and saturated aliphatic triols, wherein the aliphatic chain contains up to 4 carbon atoms. Examples are: ethanol, 1,2-butanediol, methanol, 1,2,3-butanetriol.

Examples of carbonates which can be used are: tetritol mono and biscyclic carbonates, glycerol cyclic carbonate, hexitol mono, bis and triscyclic carbonates, hexanetetrol mono and biscarbonate, butanetriol cyclic carbonate and heptanetriol cyclic carbonate.

The preparation of the hydroxyl substituted cyclic ketals described above and disclosed in U.S. Pat. application Ser. No. 873,660, which are used as precursors in the preparation of the compounds of the present invention, and which are herein also described as dioxolanyl alcohols, can be exemplified by the following Examples 1 to 6.

EXAMPLE 1

118 Grams glycerol carbonate (1 mole) is placed in a 500 ml three neck flask, fitted with a thermometer, magnetic stirrer, gas-inlet tube, and a condenser cooled with a dry iceisopropyl alcohol bath. Hexafluoroacetone gas is added to the vigorously stirred glycerol carbonate at 27° to 60° C. unitl 142 grams (0.85 moles) has been absorbed. The dry ice condenser is now replaced by a water condenser which is connected to a dry ice trap so that hexafluoroacetone which escapes during reaction may be condensed. The temperature is raised slowly to about 118° C. at which point $CO_2$ evolution begins. The temperature is allowed to rise to 148° C. during a 40 hour reaction period. The resulting product is mixed with water (50 ml) and the organic layer separated and diluted with chloroform. The chloroform solution is washed several times with water and 5% $NaHCO_3$ solution. Vacuum stripping gives crude 2,2-bis(trifluoromethyl)-4-hydroxymethyl-1,3-dioxolane. This is distilled at 78° – 80° C./25 mm Hg and the yield of pure product is 92%, based on utilized hexafluoroacetone. The twice distilled product has a refractive index of 1.35046 (20° C.) and upon analysis contained 47.19% fluorine, 30.02% carbon, and 2.22% hydrogen.

EXAMPLE 2

In accordance with the procedure of Example 1, 41.8 grams of ethylene glycol (glycerol carbonate is replaced with ethylene glycol) is reacted with 54 grams of hexafluoro acetone at 26°–35° C. for four hours and yields 95.8 grams of product.

8.5 grams of this hydroxyethyl hemiketal of hexafluoroacetone is then reacted with 3 grams of glycerol carbonate at 115°–141° C. for 103 hours. The yield is 66%, 2,2-bis(trifluoromethyl)-4-hydroxymethyl-1,3-dioxolane.

EXAMPLE 3

86.7 grams of dichlorotetrafluoroacetone is added dropwise to 50.7 grams of glycerol carbonate at 27°–35° C. while cooling is applied. The product is stirred at 35° C. for 1 hours. 50 ml additional glycerol carbonate is added and the temperature is raised to 115°–123° C. $CO_2$ evolution then starts and the temperature is raised to 150°–170° C. for a total period of 42 hours. The product is isolated according to Example 1 and is found to be a liquid, distilling at 119°–121°/20 mm. The refractive index is 1.41844 at 20° C. Analysis shows: hydroxyl number 190, 26.47% carbon, 2.57% hydrogen, 26.0% chlorine, and 27.5% fluorine. The product is 2,2-bis(chlorodifluoromethyl)-4-hydroxymethyl-1,3-dioxolane.

EXAMPLE 4

Cyclic carbonate of 1,2,4-butanetriol (38.4 grams) is treated with 57.9 grams of dichlorotetrafluoroacetone at 25°–40° C. The product is then reacted under reflux at 129° C. for 114 hours after 8 grams butanetriol has been added to provide a higher reaction temperature. The product isolated according to Example 1 is principally 2,2-bis(chlorodifluoromethyl)-4-(2-hydroxyethyl)-1,3-dioxolane and distills at 73°–81° C./0.15 mm and has a refractive index of 1.42180 at 20° C. Analysis shows: 29.3% carbon, 2.95% hydrogen, 25.0% fluorine, and 23.0% chlorine.

EXAMPLE 5

Glycerol carbonate (35.4 grams) is treated with 76 grams trichlorotrifluoroacetone dropwise at 26°–40° C. The hemiketal intermediate is diluted with additional glycerol carbonate (total carbonate present was 115.4 grams) and heated under reflux while the temperature gradually rises. Reaction time is 40 hours at 110°–123° C. and 48 hours at 123°–143° C. Weight loss is about 20 grams during that time. The isolated product is 2-chlorodifluoromethyl-2-fluorodichloromethyl-4-hydroxymethyl-1,3-dioxolane, found to distill at 92° C./0.20 mm and have a refractive index of 1.44885 at 20° C.

EXAMPLE 6

11.8 grams of glycerol carbonate is mixed with 36.2 grams of bis(trichlorodifluoroethyl) ketone and heated at 55° C. for 30 hours.

The reaction mixture temperature is then increased to 125° C. and reacted for an additional 25 hours. The product is predominantly 2,2-bis(trichlorodifluoroethyl)-4-hydroxymethyl-1,3-dioxolane.

Another general method of preparing the subject dioxolanyl alcohol precursors is disclosed in U.S. Pat. No. 2,925,424. This methol is based on reacting glycol half esters, e.g. chlorohydrins, with perhalogenated ketones in the presence of base.

Compounds e.g. halohydrins, pertinent to the present invention may be obtained from olefinic alcohols by reaction with hypochlorite, as illustrated by the method described in Bull. Soc. Chim. France, 1962 (177–182) or by reaction with N-bromosuccinimide by known method. Among olefinic alcohols which can thus be converted to chlorohydrins suitable as starting materials for the present invention, are the following; 2-methyl-2-propen-1-ol; 4-penten-1-ol; 4-penten-2-ol; 3-methyl-3-butene-1-ol; 3-methyl-3-buten-2-ol; 5-hexen-1-ol; 5-hexen-3-ol; 4-methyl-4-penten-2-ol; 2,3-dimethyl-3-buten-2-ol; 6-hepten-3-ol; 2-methyl-5-hexen-2-ol; 2,3-dimethyl-4-penten-2-ol; 1-octen-4-ol; 4-methyl-1-hepten-4-ol; 3-ethyl-5-hexen-3-ol; 2,3-dimethyl-5-hexen-3-ol; 1-nonen-4-ol; 2,3,4-trimethyl-5-hexen-3-ol; 9-decen-1-ol; 4-propyl-1-hepten-4-ol; 5,9-dimethyl-8-decen-3-ol; and 3,7,11,15-tetramethyl-2-hexadecen-1-ol.

The immediately above described method of preparing the subject hydroxyl substituted cyclic ketals is illustrated by reaction step III of Example 7 and by Example 8. Steps I and II of Example 7 illustrate an alternative method that can be used to prepare the desired chloroalkanediol.

EXAMPLE 7

Preparation of
2,2-bis(Trifluoromethyl)-4-(2-hydroxyethyl)-1,3-
Dioxolane

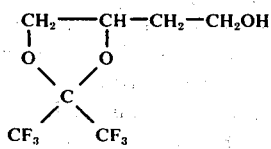

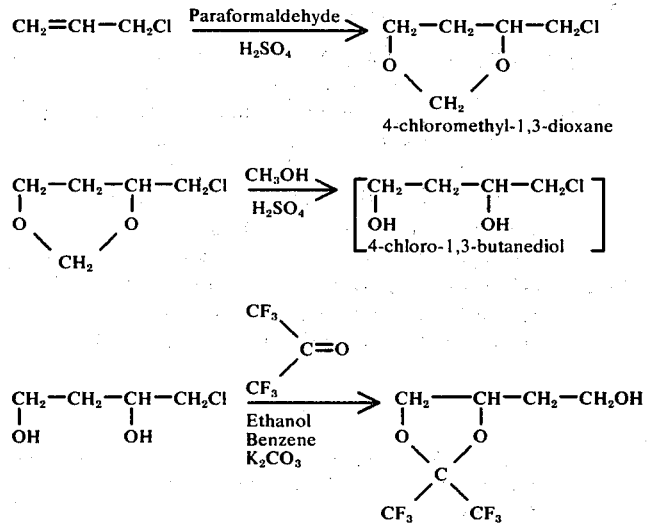

4-chloromethyl-1,3-dioxane was made in about 25% yield by a method given in the literature [C. C. Price, et al., J. Am. Chem. Soc. 72, 5335–5336 (1950)]. Because the intermediate 4-chloro-1,3-butanediol was expected to be unstable, reactions II and III above were carried out in one step without isolation of the 4-chloro-1,3-butanediol. Details of the above illustrated procedure are as follows:

A sample of 27.4 grams of 4-chloromethyl-1,3-dioxane (0.2 mols) is dissolved in 100 ml methanol and 3.6 grams concentrated sulfuric acid is added. The solution is boiled and thereby concentrated to one-half volume. This is repeated several times until hydrolysis is complete. The solvent is then evaporated at atmospheric pressure, 60 ml benzene added and the mixture stirred magnetically. Adduct of hexafluoroacetone/ethanol, containing 0.8 gram hexafluoroacetone per gram, is then added (52 grams = 0.225 mols), followed by 26.0 grams potassium carbonate (0.19 mols). The mixture is stirred at room temperature for 48 hours. The product is partitioned with the aid of 100 ml water and 40 ml benzene. The aqueous phase is extracted two times with 50 ml each of benzene and the benzene phases combined. The benzene phase is washed three times with 50 ml 5% sodium carbonate solution and three times with 100 ml of water. Benzene is evaporated under moderate vacuum at 40°–50° C. and 27.3 grams product (53.7% yield) is obtained. The product, 2,2-bis(trifluoromethyl)-4-(2-hydroxyethyl)-1,3-dioxolane is distilled at 94°–96° C./18 mm Hg. Yield of distilled product is 45%. The refractive index is 1.36053 (20° C.). Analysis of twice distilled product is as follows:

| Found: | | | Calculated: | |
|---|---|---|---|---|
| C | - | 33.18% | | 33.08% |
| H | - | 3.44% | | 3.17% |
| F | - | 44.40% | | 44.86% |

Purity was checked by gas liquid chromatography and thin layer chromatography (100%). Structure was confirmed by mass spectrometry.

EXAMPLE 8

α-Ethyl-γ,5,5-Trimethyl-2,2-Bis(Trifluoromethyl)-1,3-
Dioxolane-4-Pentanol

I.

II.

III.

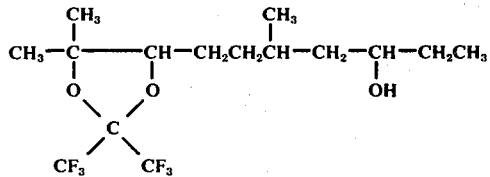

A sample of 0.1 mol 5,9-dimethyl-8-decen-3-ol is converted to the 8,9-chlorohydrin by the method described in Bull. Soc. Chim. France, 1962 (177–182). The reaction is carried out in aqueous solution in the presence of monopotassium phosphate and hypochlorite solution below a temperature of 5° C. The product is purified by extraction with water and is dissolved in about 3 parts benzene. Adduct of hexafluoroacetone-ethanol, containing about 0.8 grams hexafluoroacetone per gram, is then added (50% excess, 0.15 mols). The solution is vigorously stirred in the presence of finely ground potassium carbonate (0.15 mols) for 48 hours at room temperature. The product is partitioned between benzene and water and the benzene layer washed several times with 5% sodium carbonate solution and water. Evaporation of solvent yields the product. This may be purified by distillation in high vacuum.

U.S. Pat. No. 3,488,335, issued Jan. 6, 1970, also discloses a method of preparing 4-hydroxyl substituted dioxolane compounds which can be used as precursors in the preparation of some of the compounds of the present invention. This patent discloses compounds coming within the structure

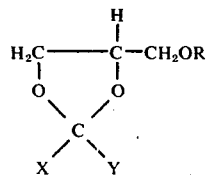

where X and Y can be perfluoroalkyl or perchlorofluoroalkyl, both of 1 through 5 carbon atoms and R can be hydrogen. Illustrative of the perchlorofluoroalkyl radicals in the X and Y positions are
— $CF_2Cl$
— $CCl_2F$
— $CF_2CF_2Cl$ The novel compounds of the present invention are prepared by several different reactions involving reacting one of the above defined hydroxyl derivatives of perhalogenated dioxolane compounds (herein also described as dioxolanyl alcohols) with one or more suitable reactants.

The compounds of the present invention wherein $R_6$ is

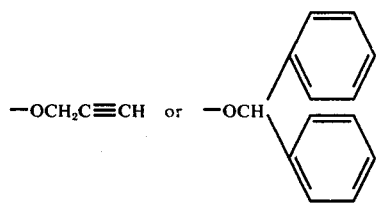

Williamson ether synthesis employing a suitable dioxolanyl alcohol, an alkynyl or arylalkyl halide and a source of alkali. In particular it has been determined that a convenient source of alkali is a sodium hydride dispersion in mineral oil. This reaction can be represented by the following general equations:

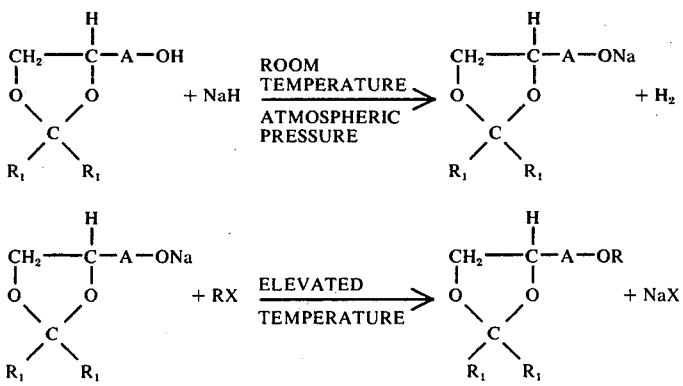

X in the above formula denotes a halogen atom having an atomic weight of at most about 80 and R is a suitable alkynyl or arylalkyl radical. $R_1$ and A are the same as defined above in relation to formula (1). The above series of reactions are carried out using essentially equal mol ratios of reactants. An excess of halide can be used if indicated. In general reaction (II) above is carried out at atmospheric pressure at a temperature within the range of about 40° C. to 150° C. depending on the boiling point of the halide reactant or the solvent used. For example, toluene can be used as a reaction solvent. The above prepared products are generally purified by distillation.

The carbamate derivatives of the present invention where

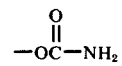

can be readily prepared by the procedure of Loew and Komendy [J. Org. Chem. 28, 3421 (1963)]. This procedure involves reacting approximately one mol of one of the above described suitable dioxolanyl alcohols in an appropriate solvent such as methylene dichloride, with about two mols of sodium cyanate followed by the slow addition of about two mols of a strong acid such as trifluoroacetic acid. This reaction can be represented by the following general equation:

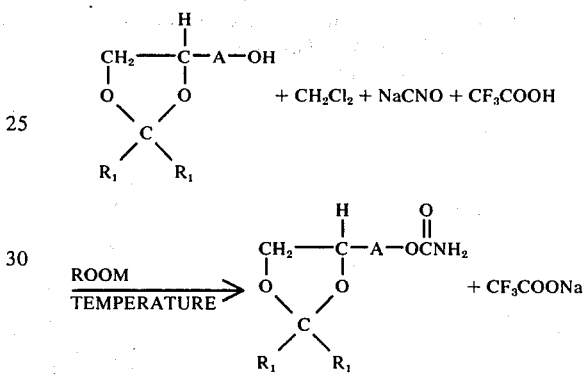

A and $R_1$ are the same as defined herein above in relation to formula (1). This reaction can be carried out at atmospheric pressure at a temperature within the range of from about 20° C. to the boiling point of methylene dichloride. The subject carbamates if a solid, can be recrystallized from an aromatic solvent or a lower alkanol. If a liquid, it can be purified by extraction or chromatography.

The nitrate compounds of the present invention are readily prepared by standard nitration procedure. A suitable dioxolanyl alcohol, as described above, is reacted with a mixture of nitric acid and acetic anhydride at room temperature or below. This reaction can be represented by the following general equation:

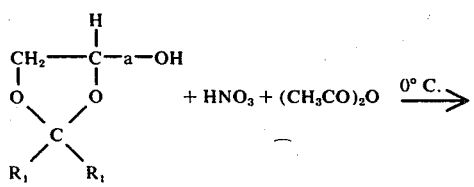

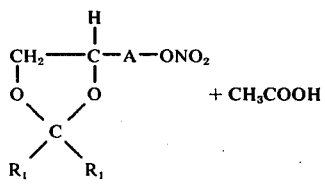

A and $R_1$ are the same as defined above in relation to formula (1). The subject nitrates can be purified by aqueous washing and treatment with activated carbon.

The subject azide derivatives of the present dioxolanyl compounds can be prepared by displacement of an ester group by an azide anion. This reaction can readily be carried out with about an equal mol ratio of reactants in a polar solvent, such as dimethylformamide, at its boiling point or just below the boiling point of the polar solvent used. This reaction can be represented by the following equation:

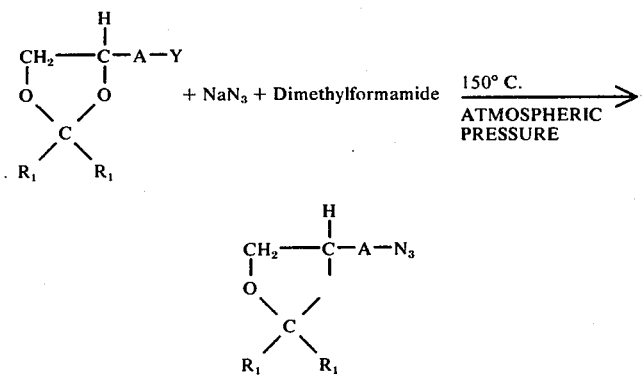

Y in the above formula is a halogen such as chlorine or

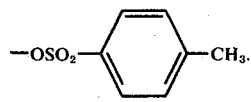

A and $R_1$ are as defined hereinabove in relation to formula (1). The present azide compounds can be purified by vacuum distillation.

The subject ester derivatives, for example, where $R_6$ is $$-OSO_2-\text{\raisebox{0pt}{\phantom{}}}-CH_3$$

can be readily prepared by reacting about one mol of the acid chloride with about one mol of a suitable dioxolanyl alcohol in the presence of pyridine as represented by the following general equation:

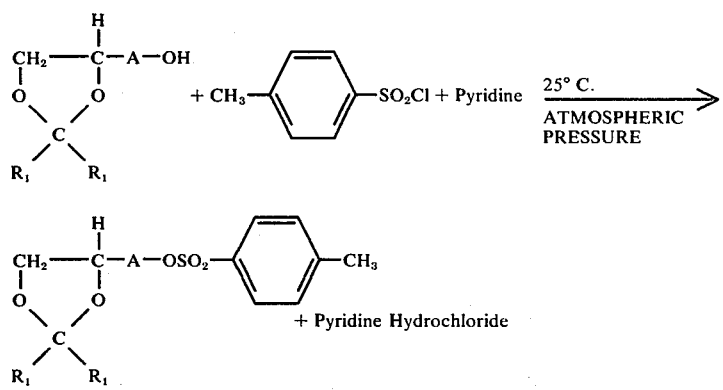

A and $R_1$ are as defined above in relation to formula (1). The subject ester derivatives can be purified by recrystallization from a lower alkanol or aromatic solvent.

The N-substituted carbamate compounds of the present invention can be readily prepared by reacting one of the above described dioxolanyl alcohols depending on the product desired, with an equal mol weight of a suitable isocyanate compound. The reaction may be carried out with or without the use of an additional reaction medium. If a reaction solvent is indicated one such as benzene can be used and the reaction is carried out at about the boiling point of benzene. Among the isocyanate reactants that can be used are p-chlorophenyl isocyanate, isopropyl isocyanate, cyclohexyl isocyanate and p-tolyl isocyanate.

It will be obvious to those skilled in the art that the above described methods of preparing the subject 4-substituted perhalogenated dioxolane compounds are also directly applicable to the preparation of the 4- and 5-substituted dioxolanes by simple replacement of the initial dioxolane reactant with a suitable difunctional initial reactant and obvious adjustment of the mol concentration of reactants so as to provide for double substitution. For example, a suitable 4,5-bis(hydroxyalkyl) substituted perhalogenated dioxolane can be used as the initial reactant where indicated.

Among the novel substituted halogenated dioxolane compounds of the present invention are, for example, 2,2-bis(chlorodifluoromethyl)-4-carbamoyloxymethyl-1,3-dioxolane; 2,2-bis(trifluoromethyl)-4-diphenylmethoxymethyl-1,3-dioxolane; 2,2-bis(trifluoromethyl)-4-(2-propynyloxymethyl)-1,3-dioxolane; 2,2-bis(trifluoromethyl)-4-(N-phenylcarbamoyloxymethyl)-1,3-dioxolane; 2,2-bis(trifluoromethyl)-4-carbamoyloxymethyl-1,3-dioxolane; 2,2-bis(trifluoromethyl)-4-azidomethyl-1,3-dioxolane; 2,2-bis(trifluoromethyl)-1,3-dioxolan-4-ylmethyl p-toluenesulfonate; 2,2-bis(chlorodifluoromethyl)-1,3-dioxolan-4-ylmethyl nitrate; 2-chlorodifluoromethyl-2-dichlorofluoromethyl-4-carbamoyloxymethyl-1,3-dioxolane; 2,2-bis(trifluoromethyl)-4-(3-carbamoyloxypropyl)-1,3-dioxolane; 2,2-bis(trifluoromethyl)-4-(6-carbamoyloxyhexyl)-1,3-dioxolane; 2,2-bis(trifluoromethyl)-4,5-bis(2-carbamoyloxyethyl)-1,3-dioxolane; 2,2-bis(trifluoromethyl)-4-(3-carbamoyloxypropyl)-5-methyl-1,3-dioxolane; 2-tribromomethyl-2-trifluoromethyl-4-carbamoyloxymethyl-1,3-dioxolane; 2-chlorodifluoromethyl-2-dichlorofluoromethyl-4-(2-carbamoyloxyethyl)-1,3-dioxolane; 2,2-bis(chlorodifluoromethyl)-4-(3-carbamoyloxypropyl)-1,3-dioxolane; 2,2-bis(trifluoromethyl)-4-(10-carbamoyloxydecyl)-1,3-dioxolane; 2,2-bis(trifluoromethyl)-4,5-bis(N-phenylcarbamoyloxyethyl)-1,3-dioxolane; 2,2-bis(trifluoromethyl)-4-(2-azidoethyl)-1,3-dioxolane.

The following examples will further serve to illustrate the preparation of the compounds of the present invention.

EXAMPLE 9

α-Ethyl-γ,5,5-Trimethyl-2,2-Bis(Trifluoromethyl)-1,3-Dioxolane-4-Pentanol Carbamate

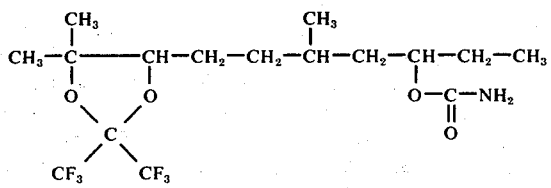

A sample of 0.1 mol of α-ethyl-γ,5,5-trimethyl-2,2-bis(trifluoromethyl)-1,3-dioxolane-4-pentanol (product of Example 8) is dissolved in 5 parts methylene dichloride and treated with 0.2 mols sodium cyanate and, dropwise, with 0.2 mols trifluoroacetic acid. The reaction mixture is stirred for 24 hours at 35°–40° C., filtered, and the filtrate washed several times with water until neutral. Evaporation of solvent from the filtrate yields the product. The product is purified by passage through a column of silica gel and elution by benzene and methanol.

EXAMPLE 10

2,2-Bis(Chlorodifluoromethyl)-1,3-Dioxolan-4-ylmethyl Nitrate 34 ml nitric acid (96%) is added slowly to 43 ml chilled acetic anhydride. Then, 14.8 grams of 2,2-bis(chlorodifluoromethyl)-4-hydroxyethyl-1,3-dioxolane, is added dropwise with magnetic stirring over a 30 minute period to the chilled mixed acid (0° to −10° C.). An additional 25 minutes of stirring is allowed. The reaction mixture is drowned in 250 ml of cold tap water forming a small lower liquid layer. Ether extraction (3 × 75 ml) removed the lower layer and all of the yellow coloration. The ether solution is washed several times with water and then dried over $Na_2SO_4$, filtered and evaporated on a rotary evaporator. The cloudy residue is redissolved in ether, treated with $Na_2SO_4$, decanted and evaporated as before. The bright yellow liquid is redissolved in ether and treated with activated carbon (DARCO G-60), then filtered (colorless), and reevaporated to yield the above named product.

Analysis Found: N, 4.15%. Calculated for $C_6H_xCl_2F_4NO_5$ (M.W. 318.02): N, 4.40%.

EXAMPLE 11

2,2-Bis(Trifluoromethyl)-1,3-Dioxolan-4-ylmethyl p-Toluenesulfonate 2,2-bis(trifluoromethyl)-4-hydroxymethyl-1,3-dioxolane, 30.0 grams (0.125), is dissolved in 40 ml pyridine and 26.2 grams p-toluenesulfonyl chloride is added. The mixture is held at room temperature for 16 hours. The product is dissolved in chloroform, extracted with water and sodium carbonate, and the solvent evaporated. The resulting product is then recrystallized in isopropyl alcohol to yield 2,2-bis(trifluoromethyl)-1,3-dioxolan-4-ylmethyl p-toluenesulfonate (m.p. 57°–58.5° C.)

Analysis Found: (In Percent) C, 39.68; H, 3.10; F, 28.90; S, 8.15. Calculated for $C_{13}H_{12}F_6O_5S$ (M.W. 394.3): C, 39.60; H, 3.07; F, 28.91, S, 8.13.

EXAMPLE 12

2,2-Bis(Trifluoromethyl)-4-Azidomethyl-1,3-Dioxolane

A sample of 14.00 grams of 2,2-bis(trifluoromethyl)-4-tosyloxymethyl-1,3-dioxolane (m.p. 58°–60° C.) is dissolved in 40 ml of dimethylformamide and 4.85 grams $NaN_3$ is added. The mixture is stirred magnetically at 140°–149° C. for 3.5 hours. The product is diluted with benzene and filtered. The filtrate is washed thoroughly with water, vacuum-stripped and distilled. The product, 2,2-bis(trifluoromethyl)-4-azidomethyl-1,3-dioxolane, has a boiling point of 78° C./20 mm Hg and a refractive index of 1.37447 at 20° C.

Analysis Found: (In Percent) C, 26.95; H, 1.73; N, 16.06. Calculated for $C_6H_5F_6N_3O_2$ (M.W. 265.1): C, 27.18; H, 1.90; N, 15.84.

EXAMPLE 13

2,2-Bis(Trifluoromethyl)-4-Carbamoyloxy-methyl-1,3-Dioxolane

A mixture of 15 grams of 2,2-bis(trifluoromethyl)-4-hydroxymethyl-1,3-dioxolane (0.0625 mols), 8.12 grams NaOCN (0.125 mols), and 75 ml methylene dichloride is stirred at 25°–35° C. while 14.3 grams trifluoroacetic acid is added dropwise. The mixture is stirred for 16 hours at 40° C. The product is filtered and the filter cake washed with methylene dichloride. The filtrate is washed with water and dried over $Na_2SO_4$ prior to vacuum-stripping. The reaction product is recrystallized from 1 part benzene to yield 2,2-bis(trifluoromethyl)-4-carbamoyloxymethyl-1,3-dioxolane (m.p. 52°–54° C.)

Analysis Found: (In Percent) C, 29.77; H, 2.65; F, 40.40; N, 4.92. Calculated for $C_7H_7F_6NO_4$ (M.W. 283.13): C, 29.69; H, 2.49; F, 40.26; N, 4.94.

EXAMPLE 14

2,2-Bis(Trifluoromethyl)-4-(N-phenylcarbamoyloxymethyl)-1,3-Dioxolane 2,2-Bis(trifluoromethyl)-4-hydroxymethyl-1,3-dioxolane 60 grams, (0.25 mols), is mixed with 28.3 grams (0.24 mols) of phenyl isocyanate under a reflux condenser and drying tube. The reaction mixture is heated to 75°–80° C. for 17 hours. The product solidifies after standing at room temperature. It is taken up in 1 part hot benzene and filtered hot (insolubles: 3.6 grams). One part hexane is added to the filtrate and the product crystallized at 0° C. Filtration, drying and solvent washing with hexane-benzene gives a white crystalline product. The filtrate is evaporated and gives 21.2 grams solids. This is washed with benzene-hexane, dissolved hot, treated with activated carbon, and crystallized at 0° C. Both crystalline crops are combined and analyzed after vacuum drying at 50° C. for 24 hours. The product is identified as 2,2-bis(trifluoromethyl)-4-(N-phenylcarbamoyloxymethyl)-1,3-dioxolane (m.p. 71°–72.5° C.).

Analysis Found: (In Percent) C, 43.42; H, 2.91; F, 31.65; N, 3.86. Calculated for $C_{13}H_{11}F_6NO_4$ (M.W. 359.2): C, 43.45; H, 3.09; F, 31.74; N, 3.90.

EXAMPLE 15

2,2-Bis(Trifluoromethyl)-4-(2-Propynyloxymethyl,-1,3-Dioxolane

A solution of 2,2-bis(trifluoromethyl)-4-hydroxymethyl-1,3-dioxolane, 12.0 grams (0.05 mols) in 50 ml toluene is prepared. 2.24 Grams of sodium hydride-mineral oil (53.5% active, 0.05 mols) is added at 24°–33° C. The resulting mixture is stirred until foaming subsided. Then excess propargyl bromide (15.6 ml, calculated 3.9 ml) is added and the mixture heated at 55°–65° C. for about 6.5 hours.

The resulting solution is filtered, washed with water, clarified by filtration through Super Cel, and vacuum-stripped (terminal 70° C./70 mm Hg).

The reaction product is distilled at 48° C./0.2 mm Hg in a 3 inch column filled with stainless steel packing to yield 2,2-bis(trifluoromethyl)-4-(2-propynyloxymethyl)-1,3-dioxolane.

Analysis Found: (In Percent) C, 39.09; H, 3.29; F, 41.14. Calculated for $C_9H_8F_6O_3$ (M.W. 278.15): C, 38.85; H, 2.9; F, 41.0, Refractive Index: 1.36986 (20° C.)

EXAMPLE 16

2,2-Bis(Trifluoromethyl)-4-Diphenylmethoxymethyl-1,3-Dioxolane

A sample of 12 grams (0.05 mols) of 2,2-bis(trifluoromethyl)-4-hydroxymethyl-1,3-dioxolane in 50 ml toluene is treated with 1.93 grams sodium hydride - mineral oil (53.4%, 0.043 mols) at 25°–33° C. The sodium salt is stirred for 2 hours at 35° C. Benzhydryl bromide, 10.6 grams, (0.043 mols) is added at 37° C. and then the temperature is raised to 75°–95° C. for 3 hours. The mixture is filtered and the filtrate washed with water. Vacuum-stripping gives an oil which is dissolved in methanol and clarified by filtration through Super Cel. Yield of product is 17.0 grams at this point. A forerun is distilled in a 4 inch column filled with stainless steel packing, the remainder without packed column. The product obtained is distilled at 137° C. under 0.45 mm of mercury pressure to yield 2,2-bis(trifluoromethyl)-4-diphenylmethoxymethyl-1,3-dioxolane.

Analysis Found: (In Percent) C, 55.99; H, 4.45; F, 28.51. Calculated for $C_{19}H_{16}F_6O_3$ (M.W. 406.32); C, 56.1; H, 3.97; F, 28.1. Refractive Index: 1.48003 (20° C.).

EXAMPLE 17

2,2-Bis(Chlorodifluoromethyl)-4-Carbamoyloxymethyl-1,3-Dioxolane

A sample of 15 grams of 2,2-bis(chlorodifluoromethyl)-4-hydroxymethyl-1,3-dioxolane (0.055 mols) is dissolved in 75 ml methylene chloride and 7.16 grams of sodium cyanate (0.11 mols) is added. Trifluoroacetic acid, 12.6 grams, (0.11 mols) is added dropwise with stirring at 23°–33° C. The temperature is then raised to 40° C. and stirring continued for 18 hours. The product is filtered and the filtrate washed with water until neutral. Vacuum stripping gives a quantitative yield of crude products which solidified partly. Filtration and recrystallization from a mixture of benzene-hexane and once from cyclohexane yields 2,2-bis(chlorodifluoromethyl)-4-carbamoyloxymethyl-1,3-dioxolane (m.p. 56°–57° C.)

Analysis Found: (In Percent) C, 27.88; H, 2.28; Cl, 22.88; F, 24.34; N, 4.44. Calculated for $C_7H_7Cl_2F_4NO_4$ (M.W. 316.03): C, 27.16; H, 2.28; Cl, 22.90; F, 24.55; N, 4.43.

EXAMPLE 18

2,2-Bis(Chlorodifluoromethyl)-4-[N-(p-chlorophenyl)carbamoyloxymethyl]-1,3-Dioxolane 2,2-Bis(chlorodifluoromethyl)-4-hydroxymethyl-1,3-dioxolane, 68.0 grams, (0.25 mol) is treated with 36.8 grams (0.24 mol) of p-chlorophenyl isocyanate at 75°–80° C. for a period of 15–20 hours. The product, 2,2-bis(chlorodifluoromethyl)-4-[N-(p-chlorophenyl)-carbamoyloxymethyl]-1,3-dioxolane, is purified by crystallization from benzene or a mixture of benzene and hexane and may be decolorized by treatment with activated carbon.

The procedure of Example 18 may be used for the preparation of other N-substituted carbamates, where isopropyl isocyanate, cyclohexyl isocyanate and p-tolyl isocyanate are substituted for p-chlorophenyl isocyanate.

EXAMPLE 19

α,α,5-Trimethyl-2,2-bis(Chlorodifluoromethyl)1,3-Dioxolane-4-Methanol Carbamate

A solution of 31.5 grams (0.1 mol) of α,α,5-trimethyl-2,2-bis(chlorodifluoromethyl)-1,3-dioxolane-4-methanol in 180 ml methylene dichloride is treated with 13.0 grams sodium cyanate (0.2 mol) while 22.8 grams of trifluoroacetic acid (0.2 mol) is added dropwise. The reaction is carried out at 25°–35° C. for 24 hours. After the reaction is completed, a small amount of water is added to dissolve salts and the methylene dichloride solution is separated and extracted once more with water. Vacuum stripping yields the product α,α,5-trimethyl-2,2-bis(chlorodifluoromethyl)-1,3-dioxolane-4-methanol carbamate. The product is purified by crystallization from a mixture of benzene and hexane.

The dioxolanyl alcohol used above in this example can be obtained by the method of U.S. patent application Ser. No. 873,660 or by the reaction of the oxide alcohol V with the appropriate perhaloketone according to the method of U.S. Pat. No. 3,488,335 as represented by the following general equation:

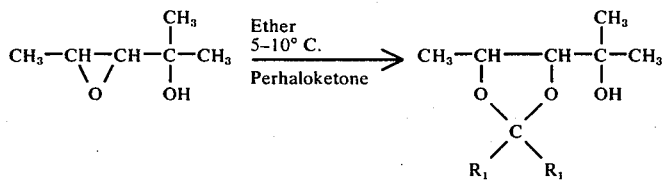

wherein $R_1$ is the desired perhalogenated alkyl radical.

EXAMPLE 20

2,2-Bis(Chlorodifluoromethyl)-4,5-bis(1-carbamoyloxyethyl-1,3-Dioxolane

A solution of 33.1 grams (0.1 mol) of 2,2-bis(chlorodifluoromethyl)-4,5-bis(1-hydroxyethyl)-1,3-dioxolane in 200 ml methylene dichloride is treated with 13.0 grams sodium cyanate (0.2 mol) and 22.8 grams trifluoroacetic acid (0.2 mol) in the same way as in Example 19. The product, 2,2-bis(chlorodifluoromethyl)-4,5-bis(1-carbamoyloxymethyl)-1,3-dioxolane, is isolated and purified in the manner of Example 19.

The dioxolanyl alcohol used above in this example is prepared from 3-hexene-2,5-diol by the reaction represented by the following general equation:

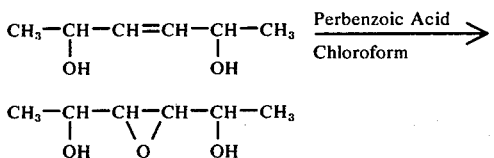

VIII

The above oxido diol (VIII) is converted to the dioxolanyl diol with the appropriate perhaloketone according to the method of U.S. Pat. No. 3,488,335.

EXAMPLE 21

1-[2,2-Bis(Chlorodifluoromethyl)-1,3-Dioxolan-4-yl] Butyl Nitrate 34 ml of nitric acid (96%) is added slowly to 43 ml distilled acetic anhydride. Then 2,2-bis(chlorodifluoromethyl)-4-(1-hydroxybutyl)-1,3-dioxolane, 17.1 grams, is added dropwise with stirring over a 30 minute period at 0° C. to −10° C. This dioxolanyl alcohol is prepared from 1,2,3-hexanetriol and the appropriate perhalogenated ketone using the method disclosed in patent application Ser. No. 873,660. An additional reaction period of 25 minutes is allowed. The reaction mixture is added to 250 ml cold water and extracted with several 75 ml portions of ether. The ether solution of product is washed thoroughly with water, treated with activated carbon and dried over sodium sulfate. Filtration and evaporation yields 1-[2,2-bis(chlorodifluoromethyl)-1,3-dioxolan-4-yl] butyl nitrate.

EXAMPLE 22

2,2-Bis(Heptafluoropropyl)-4-Carbamoyloxymethyl-1,3-Dioxolane

A solution of 44.0 grams (0.1 mol) of 2,2-bis(heptafluoropropyl)-4-hydroxymethyl-1,3-dioxolane prepared by the method disclosed in patent application Ser. No. 873,660 filed Nov. 3, 1969, in 250 ml methylene dichloride is treated with 13.0 grams of sodium cyanate while 22.8 grams trifluoroacetic acid is added dropwise. The reaction is carried out at 25°–35° C. for 24 hours. After the reaction is completed, a small amount of water is added to dissolve the salts and the methylene dichloride solution is separated and washed with water. Vacuum-stripping yields the desired product. The product, 2,2-bis(heptafluoropropyl)-4-carbamoyloxymethyl-1,3-dioxolane, is purified by crystallization from a mixture of benzene and hexane.

EXAMPLE 23

Preparation of 2,2-Bis(Trifluoromethyl)-4-(2-Carbamoyloxyethyl)-1,3-Dioxolane

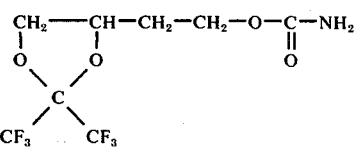

A sample of 2,2bis(trifluoromethyl)-4-(2-hydroxyethyl)-1,3-dioxolane, 10 grams (39.4 millimols), is dissolved in 50 ml methylene chloride and treated with 5.12 grams sodium cyanate and, dropwise, with 9.0 grams trifluoroacetic acid. The reaction is carried out at 25°–41° C. for 1.5 hours and at room temperature for 66 hours. The product is filtered and the filtrate washed five times with 25 ml water. Solvent is vacuum-stripped and the crude product treated at 75°–115° C./0.4 mm Hg to remove by-product and starting material. Yield of syrup product is 8.4 grams (71.5%). The product is purified by passage through a column of Silica gel and elution with benzene and methanol. Yield of pure product is 7.4 grams (63%). The refractive index is 1.38662 (20.4° C.). Analysis is as follows:

| Found: | C | - | 32.34% | Calculated: | 32.35% |
|--------|---|---|--------|-------------|--------|
|        | H | - | 2.91%  |             | 3.04%  |
|        | F | - | 38.00% |             | 38.41% |
|        | N | - | 4.79%  |             | 4.72%  |

EXAMPLE 24

2-Chlorodifluoromethyl-2-Dichlorofluoromethyl-4-Carbamoyloxymethyl-1,3-Dioxolane 20 grams of 2-chlorodifluoromethyl-2-dichlorofluoromethyl-4-hydroxymethyl-1,3-dioxolane (0.069 mol) was dissolved in 100 ml methylene dichloride. Sodium cyanate (9 grams, 0.138 mol) was added. The suspension was stirred while 15.7 grams trifluoroacetic acid was added dropwise. The reaction was carried out at 40° C. for 16 hours. The mixture was filtered and the filtrate washed with water until neutral. Removal of the solvent by vacuum-stripping gave a quantitative yield of product which partially solidified on standing. The product was filtered and recrystallized from a 1:1 mixture of benzene and cyclohexane. Yield of pure product was 12.4 grams (54%). The product was a white solid which melted at 76°–78° C.

Analysis found: (In Percent) C, 25.38; H, 2.14; Cl, 31.86; F, 17.18; N, 4.14. Calculated for $C_7H_7Cl_3F_3NO_4$ (M.W. 332.5): C, 25.29; H, 2.12; Cl, 31.99; F, 17.14; N, 4.21.

Various test procedures are used in the laboratory to test for tranquilizer activity. Among those tests used are the "Shock-Induced Aggression Test" and "The Amphetamine Toxicity Antagonism Test" which can be carried out as follows:

Shock-Induced Agression (mice)

In this procedure, two mice are placed on a grid, and the grid is electrified for two minutes. This induces the animals to engage in aggressive behavior toward each other. The amount of time spent fighting by each pair of control mice (injected with water) is compared to the amount of time spent fighting by pairs injected with the test drug. Drugs are administered orally. Tranquilizers lower fighting time by reducing aggressiveness.
Results:
  The compound, 2,2-bis(chlorodifluoromethyl)-4-carbamoyloxymethyl-1,3-dioxolane, reduced fighting time by 87% at 200 mg/kg, and by 68% at 100 mg/kg.

Amphetamine Toxicity Antagonism (mice)

In this test, ten mice are injected orally with either water (controls) or a test drug, and 1 hour later are injected intraperitoneally with amphetamine. The dose of amphetamine is one which causes death in 80–100% of control mice, by over-stimulating the sympathetic nervous system. At 2 and 4 hours after amphetamine injection, the number of animals remaining alive in each group is compared.
Results:
  The compound, 2,2-bis(chlorodifluoromethyl)-4-carbamoyloxymethyl-1,3-dioxolane, reduced amphetamine toxicity by 100 % at 200 mg/kg, and gave 90% protection at 50 mg/kg.

Evaluation in laboratory animals indicate that the present dioxolane compounds possess tranquilizer activity when administered in a therapeutically effective amount. The effectiveness and dosage required vary, as is customary in this art, with the species being treated, particular disorder being treated, weight of the animal and the route of administration. An appropriate dose and method of administration suitable for any animal susceptible to these compounds may be readily found as a simple routine determination. In accordance with the invention, the subject compounds are administered at doses from about 1.0 milligram to 500 milligrams per kilogram body weight 1 to 4 times a day. As indicated above, desirably effective dosage will vary depending upon the species of animal and other above-stated variables. For example, a preferred dosage range for rats of 2,2-bis(trifluoromethyl)-4-(2-carbamoyloxyethyl)-1,3-dioxolane and 2,2-bis(chlorodifluoromethyl)-4-carbamoyloxymethyl-1,3-dioxolane is from about 50 to 325 milligrams per kilogram body weight by intraperitoneal injection. A preferred oral dose range for monkeys of 2,2-bis(chlorodifluoromethyl)-4-carbamoyloxymethyl-1,3-dioxolane is from about 50 to 100 milligrams per kilogram body weight. A preferred oral dose range for monkeys of 2-chlorodifluoromethyl-2-dichlorofluoromethyl-4-carbamoyloxymethyl-1,3-dioxolane is from about 100 to 200 milligrams per kilogram body weight. Further, a preferred oral dose range for mice of 2,2-bis(trifluoromethyl)-4-carbamoyloxymethyl-1,3-dioxolane and 2,2-bis(chlorodifluoromethyl)-1,3-dioxolan-4-ylmethyl nitrate is from about 200 to 300 milligrams per kilogram body weight. A preferred oral dose range for mice of 2,2-bis(chlorodifluoromethyl)-4-carbamoyloxymethyl-1,3-dioxolane is from about 50 to 300 milligrams per kilogram body weight.

As the compounds within the scope of this invention are effective upon oral administration they can be compounded in any suitable oral dosage form as in tablet, capsule, syrup, elixir, suspension or other solid or liquid forms that can be prepared by procedures well known in the art. Thus, the subject novel compounds can be mixed with a suitable diluent such as lactose or kaolin and encapsulated; or they can be combined with suitable binding agents and expanding agents and compressed into tablets. In addition a liquid pharmaceutical may be obtained by dissolving or suspending novel compounds of this invention with a suitable flavored liquid. The present compounds are also considered active upon parenteral and rectal administration.

Examples of formulation for preparing tablets, capsules, liquids, parenterals and suppositories containing the novel dioxolane compounds of the present invention are described below. Obviously, it will be recognized by one skilled in the present art that the following formulations represent only one method for preparing such pharmaceutical compositions and obviously the size of the tablet or capsule or the strength of the dosage form may be suitably varied in order to satisfy the particular requirements such as dosage level indicated. For example, each dosage unit may conveniently contain from about 15 mg to 5000 mg of the active ingredient admixed with a diluent amount of a pharmaceutically acceptable carrier. Any of the well known suitable pharmaceutical carriers can be used to provide acceptable dosage forms so as to provide an effective amount or therapeutically effective amount of the compound to be administered.

| Tablet Containing 100 mg of 2,2-Bis(Trifluoromethyl)-4-(N-phenylcarbamoyloxymethyl)-1,3-Dioxolane | 1000 Tablets (Grams) |
|---|---|
| 2,2-Bis(Trifluoromethyl)-4-(N-phenyl-carbamoyloxymethyl-1,3-Dioxolane | 100 |
| Starch | 80 |
| Powdered Lactose | 80 |
| Talc | 20 |
| Weight of granulation | 280 |

Combine all ingredients, mix and then compress into slugs. The slugs should then be ground to form granules that will pass through a 14–16 mesh screen. The granules may then be recompressed into tablets using a suitable compression mold to form tablets, each weighing 280 mg.

| Capsule Containing 200 mg of 2,2-Bis(Chlorodifluoromethyl)-4-Carbamoyloxymethyl-1,3-Dioxolane | |
|---|---|
| 2,2-Bis(Chlorodifluoromethyl)-4-Carbamoyloxymethyl-1,3-Dioxolane | 200 mg |
| Powdered Lactose | 100 mg |
| D.T.D. Capsules No. 1000 | |

Mix the ingredients so as to evenly distribute the active ingredient throughout the lactose. Pack the powder into No. 1 empty gelatin capsule.

| Suspension Containing 50 mg per 5 cc of 2,2-Bis(Trifluoromethyl)-4-Carbamoyloxymethyl-1,3-Dioxolane | |
|---|---|
| 2,2-Bis(Trifluoromethyl)-4-Carbamoyloxymethyl-1,3-Dioxolane | 10 grams |
| Tragacanth | 50 grams |
| Amaranth | 10 grams |
| Syrup Wild Cherry | 60 ml |
| Distilled Water q.s. | 1000 ml. |

Hydrate the tragacanth with sufficient water to form a smooth paste and to this add the 2,2-bis(trifluoromethyl)-4-carbamoyloxymethyl-1,3-dioxolane, followed by the amaranth which has been previously dissolved in water. Then add the syrup of wild cherry and add distilled water to make 1000 ml.

Injectable Containing 5 mg of
2,2-Bis(Trifluoromethyl)-4-Azidomethyl-1,3-Dioxolane Per Milliliter Suitable for Intramuscular, Intraperitoneal or Subcutaneous Injection

| Injectable Containing 5 mg of 2,2-Bis(Trifluoromethyl)-4-Azidomethyl-1,3-Dioxolane Per Milliliter Suitable for Intramuscular, Intraperitoneal or Subcutaneous Injection | |
|---|---|
| 2,2Bis(Trifluoromethyl)-4-Azidomethyl-1,3-Dioxolane | 5.0 grams |
| Chlorobutanol | 3.0 grams |
| Propylene Glycol | 20.0 ml |
| Water for injection q.s. | 1000.0 ml |

Combine the above ingredients, clarify by filtration, fill into vials, seal and autoclave.

| Suppository Containing 200 mg of 2,2-Bis(Trifluoromethyl)-4-(2-Carbamoyloxyethyl)-1,3-Dioxolane | |
|---|---|
| 2,2-bis(Trifluoromethyl)-4-(2-Carbamoyloxyethyl)1,3-Dioxolane | 0.2 gram |
| Cocoa Butter | 1.8 grams |
| Make of such No. 100 | |

Melt the cocoa butter and disperse the 2,2-bis(trifluoromethyl)-4-(2-carbamoyloxyethyl)-1,3-dioxolane in the molten mass and stir until uniform. Pour the resulting molten mass into suppository mold and chill. Remove suppositories from mold and package.

What is claimed is:

1. A compound of the formula

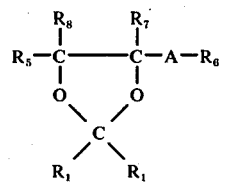

wherein each $R_1$ is an independently selected perhalogenated alkyl radical, A is an alkylene radical, $R_6$ is selected from the group consisting of $-ONO_2$ $-OCH_2C\equiv CH$

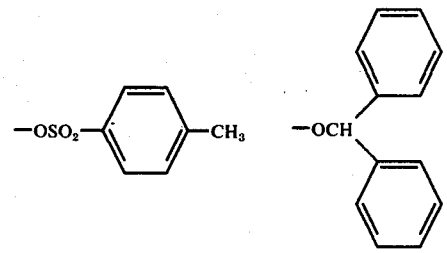

$R_5$ is selected from the group consisting of hydrogen, alkyl and $-A-R_6$, and $R_7$ and $R_8$ are independently selected from the group consisting of hydrogen and lower alkyl radicals and with the further proviso that $R_6$ can be a hydroxyl radical when either $R_7$ or $R_8$ is an alkyl radical or when the total number of carbon atoms in the alkylene or alkyl chains contained in the radicals represented by $-A-$ and $R_5$ combined equal 6 or more.

2. A compound of claim 1 wherein the $R_1$ radical contains from 1 to 7 carbon atoms.

3. A compound of claim 2 wherein A is a lower alkylene radical containing from 1 to 6 carbon atoms.

4. A compound of claim 3 wherein $R_5$ is hydrogen.

5. A compound of claim 3 wherein $R_5$ is a lower alkyl radical containing from 1 to 6 carbon atoms.

6. A compound of claim 1 which is 2,2-bis(chlorodifluoromethyl)-1,3-dioxolan-4-ylmethyl nitrate.

7. A compound of claim 1 which is 2,2-bis(trifluoromethyl)-1,3-dioxolan-4-ylmethyl nitrate.

8. A compound of claim 1 which is 1-[2,2-bis(-chlorodifluoromethyl)-1,3-dioxolan-4-yl] butyl nitrate.

9. A compound of claim 1 which is 2,2-bis(heptafluoropropyl)-1,3-dioxolan-4-ylmethyl nitrate.

10. A compound of claim 1 which is 1-[2,2-bis(trichloromethyl)-1,3-dioxolan-4-yl]pentyl nitrate.

11. A compound of claim 1 which is 2,2-bis(trifluoromethyl)-1,3-dioxolan-4-ylmethyl p-toluenesulfonate.

12. A compound of claim 1 which is 2,2-bis(trifluoromethyl)-4-(2-propynyl-oxymethyl)-1,3-dioxolane.

13. A compound of claim 1 which is 2,2-bis(trifluoromethyl)-4-diphenyl-methoxymethyl-1,3-dioxolane.

14. A composition containing a tranquilizing effective amount of the compound of claim 1 in a pharmaceutically acceptable carrier.

15. A method of tranquilizing an animal which comprises administering a tranquilizing effective amount of a compound of claim 1 to an animal susceptible thereto.

16. A method of tranquilizing a mammal comprising administering a tranquilizing effective amount of a composition of claim 14.

* * * * *

UNITED STATES PATENT AND TRADEMARK OFFICE
CERTIFICATE OF CORRECTION

PATENT NO. : 3,996,376
DATED : December 7, 1976
INVENTOR(S) : Ludwig A. Hartmann It is certified that error appears in the above-identified patent and that said Letters Patent are hereby corrected as shown below:

Column 2, line 33, after "linear" and before "alkylene" insert -- lower --.

Column 2, line 41, after "present" and before "group" insert -- preferred --.

Column 3, line 68, "polyhyric" should read -- polyhydric --.

Column 4, line 58, "leaast" should read -- least --.

Column 5, line 18, "iceisopropyl" should read -- ice-isopropyl --.

Column 5, line 20, "unitl" should read -- until --.

Column 9, line 34, before the line beginning "Williamson" insert the line -- can be conveniently prepared by the --.

Column 11, line 1,

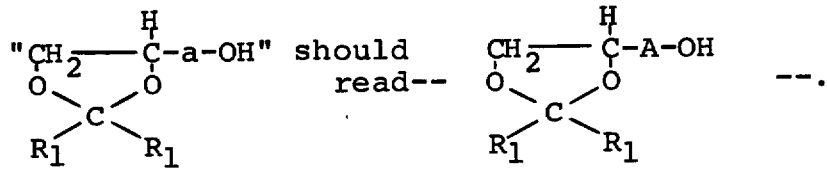

UNITED STATES PATENT AND TRADEMARK OFFICE
CERTIFICATE OF CORRECTION

PATENT NO. : 3,996,376
DATED : December 7, 1976
INVENTOR(S) : Ludwig A. Hartmann It is certified that error appears in the above-identified patent and that said Letters Patent are hereby corrected as shown below:

Column 11, line 54,

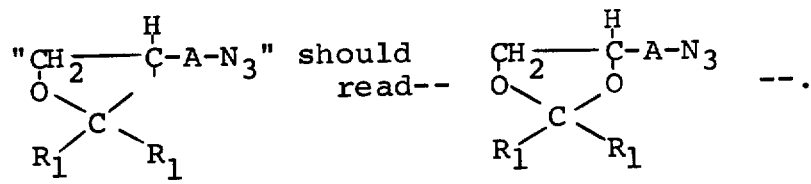

Column 14, line 12, "-hydroxyethyl-" should read -- -hydroxymethyl- --.

Signed and Sealed this

First Day of November 1977

[SEAL]

Attest:

RUTH C. MASON
Attesting Officer

LUTRELLE F. PARKER
Acting Commissioner of Patents and Trademarks